United States Patent
Demassey et al.

(10) Patent No.: US 6,579,902 B1
(45) Date of Patent: Jun. 17, 2003

(54) RIBOSE-SUBSTITUTED AROMATIC AMIDES, METHOD FOR THE PRODUCTION AND USE THEREOF AS MEDICAMENTS

(75) Inventors: Jacques Demassey, Chalifert (FR); Michel Klich, Villemomble (FR); Branislav Musicki, Paris (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/980,728

(22) PCT Filed: Apr. 18, 2000

(86) PCT No.: PCT/FR00/00999
§ 371 (c)(1),
(2), (4) Date: Jan. 9, 2002

(87) PCT Pub. No.: WO00/63222
PCT Pub. Date: Oct. 26, 2000

(30) Foreign Application Priority Data

Apr. 19, 1999 (FR) .............................. 99 04866

(51) Int. Cl.$^7$ ....................... A61K 31/35; C07D 311/02
(52) U.S. Cl. ....................... 514/456; 514/457; 549/229; 549/285
(58) Field of Search ............... 549/229, 285; 514/456, 457

(56) References Cited

U.S. PATENT DOCUMENTS 3,890,297 A   6/1975   Dolak ................... 260/210 R

FOREIGN PATENT DOCUMENTS

FR           2052923        4/1971

OTHER PUBLICATIONS

Dolak, Lester A. 'N–Acylating novenamine' (1975) corresponds to USP 3,980,297.*

Hooper, David C. et al 'Effects of novobiocin, coumermycin A1, clorobiocin, and their analogs on *Escherichia coli* DNA gyrase and bacterial growth', CA 98:104128) Antimicrob. Agents Chemother. (1982), 22(4), 662–71.*

Crow et al, "Complete . . . –Carbonate", J. Heterocycl. Chem (1999), 36(2), pp. 365–370.

Bell et al, "Design . . . Novobiocin", J. Chem. Soc., Perkin Trans. 1 (1997), (18), pp. 2789–2801.

\* cited by examiner

*Primary Examiner*—Amelia Owens
(74) *Attorney, Agent, or Firm*—Muserlian, Lucas and Mercanti

(57) ABSTRACT

Compounds of formula (I); wherein $R_1$=alkyl, alkenyl or alkynyl, O-alkyl, O-alkenyl or optionally substituted, optionally interrupted O-alkynyl; $R_2$=hydrogen or halogen; $R_3$=hydrogen, alkyl or halogen; $R_4$=NHR' or NHOR", R' or R" are identical or different and represent hydrogen, alkyl, alkenyl or alkynyl, aryl; $R_5$=hydrogen or O-alkyl; $R_6$=alkyl or $CH_2$—O-alkyl; $R_7$=hydrogen or alkyl or $R_6$ et $R_7$ form a cycle together with the carbon carrying them in addition to the addition salts thereof with bases. The compounds of formula (I) have antibiotic properties.

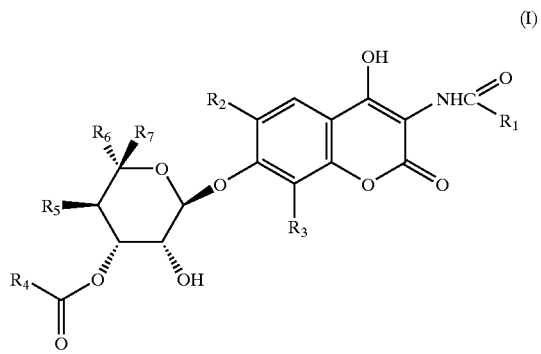

21 Claims, No Drawings

RIBOSE-SUBSTITUTED AROMATIC AMIDES, METHOD FOR THE PRODUCTION AND USE THEREOF AS MEDICAMENTS

The present invention relates to new aromatic amides substituted by a ribose, their preparation process and their use as medicaments.

A subject of the invention is the compounds of formula (I):

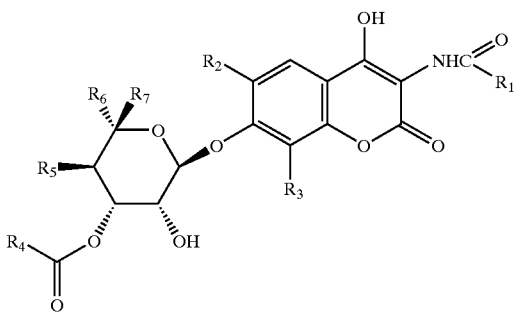

in which
- $R_1$ represents a linear, branched or cyclic alkyl, alkenyl or alkynyl, O-alkyl, O-alkenyl or O-alkynyl radical containing up to 8 carbon atoms optionally substituted by one or more halogen atoms, optionally interrupted by an oxygen, sulphur or nitrogen atom, an optionally substituted aryl or aralkyl radical containing up to 18 carbon atoms, an optionally substituted mono or polycyclic aromatic or non-aromatic heterocyclic radical, an $NH_2$, $NHalk_1$ or $NHalk_2$, $NHalk_3$ or $NHOalk_4$ radical, $alk_1$, $alk_2$, $alk_3$ and $alk_4$ representing an alkyl radical containing up to 8 carbon atoms,
- $R_2$ represents a hydrogen atom or a halogen atom,
- $R_3$ represents a hydrogen atom, an alkyl radical containing up to 8 carbon atoms or a halogen atom,
- $R_4$ represents an NHR' or NHOR" radical in which R' or R" identical or different represent a hydrogen atom, a linear, branched or cyclic alkyl, alkenyl or alkynyl radical containing up to 8 carbon atoms, an optionally substituted aryl radical containing up to 14 carbon atoms,
- $R_5$ represents a hydrogen atom or an O-alkyl radical containing up to 8 carbon atoms,
- $R_6$ an alkyl or $CH_2$—O-alkyl radical, in which alkyl represents an alkyl radical containing up to 8 carbon atoms,
- $R_7$ represents a hydrogen atom or an alkyl radical containing up to 8 carbon atoms or $R_6$ and $R_7$ form together with the carbon which carries them a ring as well as their addition salts with bases.

As examples of bases there can be mentioned the salts formed with amines such as arginine, lysine, the $Na^+$, $K^+$, $NH_3^+$, $N(alk)_3^+$ ions, $alk_3$ representing an alkyl radical containing up to 8 carbon atoms.

In the definition of the substituents:
- the alkyl, alkenyl or alkynyl radical is preferably a methyl, ethyl, propyl, isopropyl, n-butyl, isobutyl, terbutyl, decyl or dodecyl, vinyl, allyl, ethynyl, propynyl, cyclobutyl, cyclopentyl or cyclohexyl radical,
- the halogen is preferably fluorine or chlorine, or bromine,
- the aryl radical is preferably the phenyl radical.

A more particular subject of the invention is the compounds of formula (I) in which $R_1$ represents an alkyl radical containing up to 4 carbon atoms, for example

radical, the compounds of formula (I) in which $R_1$ represents a phenyl radical, the compounds of formula (I) in which $R_2$ represents a hydrogen atom, the compounds of formula (I) in which $R_3$ represents a methyl radical, the compounds of formula (I) in which $R_5$ is an $OCH_3$ radical, the compounds of formula (I) in which $R_6$ and $R_7$ represents a methyl radical of an ethyl radical as well as those in which $R_6$ and $R_7$ together with the carbon which carry them form a cyclopentyl radical.

Among the preferred compounds of the invention, there can be mentioned the compounds of formula (I) in which $R_4$ represents an $NH$—$O$—$CH_2$—$C\equiv CH$ radical.

A particular subject of the invention is the compounds the preparation of which is given hereafter in the experimental part and quite particularly the product of Examples 10 and 11. The products of general formula (I) have a very good antibiotic activity on anaerobic gram bacteria such as staphylococci, streptococci, pneumococci, enterococci, listeria.

The compounds of the invention can therefore be used as medicaments in the treatment of germ-sensitive infections and, in particular, in that of staphylococcia, such as staphylococcal septicemias, malignant facial or cutaneous staphylococcia, pyodermatitis, septic or suppurating wounds, boils, anthrax, phlegmons, erysipelas and acne, staphylococcias such as primative or post-influenzal acute angina, bronchopneumonia, pulmonary suppuration, streptococcia such as acute angina, otitis, sinusitis, scarlatina, pneumococcia such as pneumonia, bronchitis and diphtheria. The products of the present invention are also active against infections caused by germs such as Haemophilus influenzae.

A subject of the invention is therefore the compounds of formula (I) as well as their pharmaceutically acceptable salts as medicaments.

A more particular subject of the invention is as medicaments the compounds indicated above as preferred compounds.

A subject of the invention is also the pharmaceutical compositions containing as active ingredient at least one of the medicaments defined above.

These compositions can be administered by buccal, rectal, parenteral route or by local route as a topical application on the skin and the mucous membranes, but the preferred administration route is the buccal or injectable route.

They can be solids or liquids and be presented in the pharmaceutical forms commonly used in human medicine, such as for example, plain or sugar-coated tablets, gelatin capsules, granules, suppositories, injectable preparations, ointments, creams, gels; they are prepared according to the usual methods. The active ingredient(s) can be incorporated with the excipients usually used in these pharmaceutical compositions, such as talc, gum arabic, lactose, starch, magnesium stearate, cocoa butter, aqueous or non aqueous vehicles, fatty substances of animal or vegetable origin, paraffin derivatives, glycols, various wetting, dispersing or emulsifying agents, preservatives.

These compositions can also be presented in the form of a powder intended to be dissolved extemporaneously in an appropriate vehicle, for example apyrogenic sterile water.

The dose administered is variable according to the condition treated, the patient in question, the administration route and the product considered. It can be, for example, comprised between 50 mg and 3000 mg per day by oral or injectable route in adults for the preferred products.

A subject of the invention is a process for the preparation of the compounds of formula (I) characterized in that a compound of formula (II):

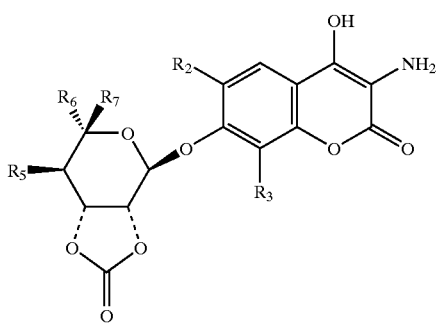

(II)

is subjected to the action of a compound of formula

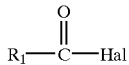

in which $R_1$ retains its previous meaning and Hal represents a halogen atom in order to obtain the compound of formula (III):

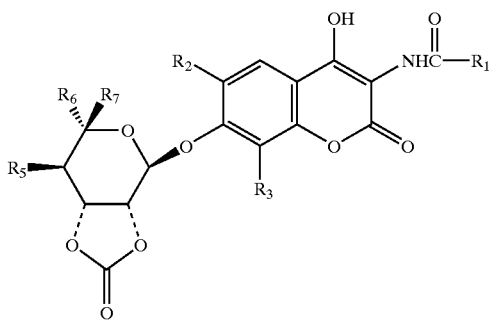

(III)

which is subjected to the action of a compound of formula $R_4H$ (IV)

in order to obtain the compound of formula

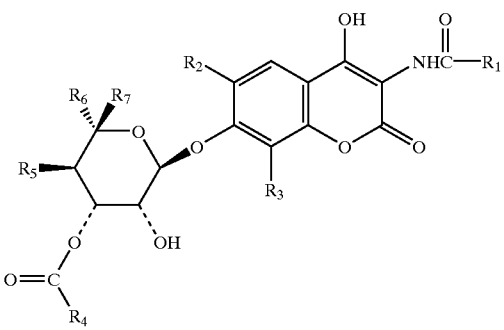

(I)

A subject of the invention is also as new chemical products, the compounds of formula (II) and (III). In a preferred embodiment, Hal is a chlorine atom.

The compounds of formula (II) used as starting products in the process according to the invention, can be prepared as indicated hereafter in the experimental part. The preparation of the compounds of formula (II) described in the experimental part can be illustrated as follows:

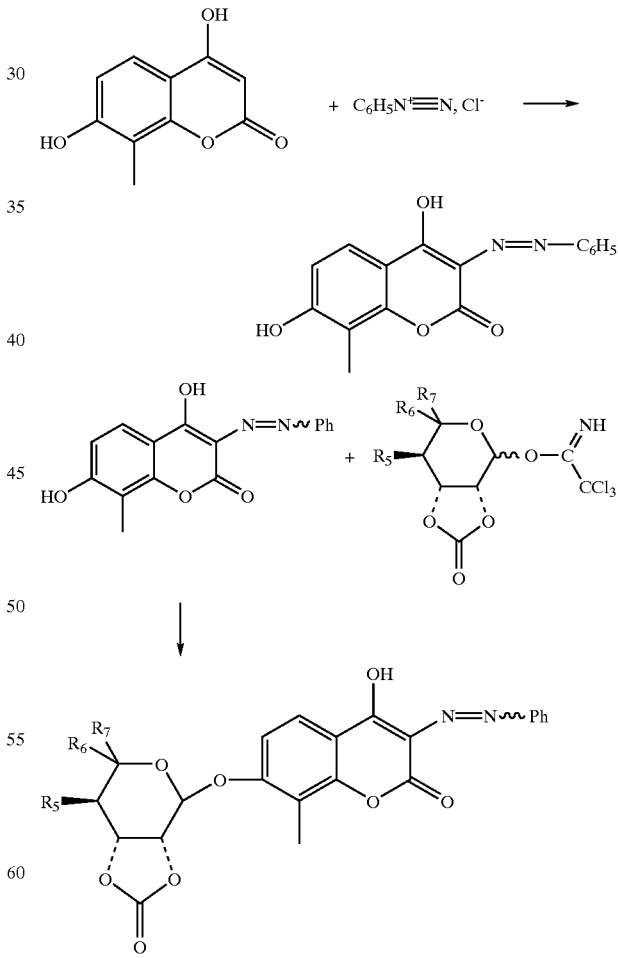

-continued

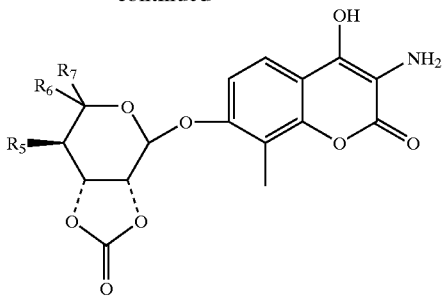

A subject of the invention is also a process characterized in that a compound of formula (V):

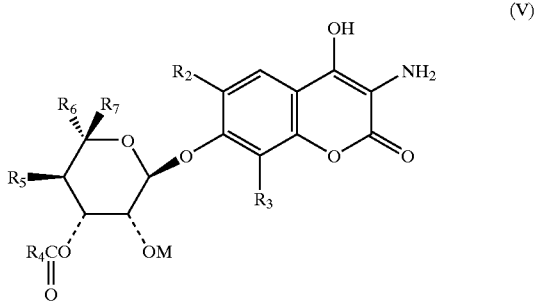

in which the substituents retain their previous meaning and OM represents a blocked hydroxyl radical, is subjected to the action of a compound of formula $R_1COHal$ in which $R_1$ retains its previous meaning and Hal represents a halogen atom, then to the action of an agent which releases the OH function in order to obtain the corresponding compound of formula (I):

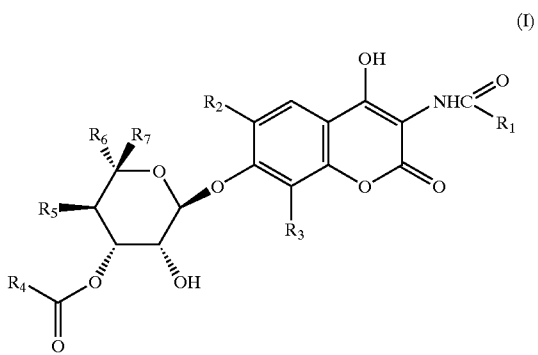

The products of formula (V) used as starting products are new products and are in themselves a subject of the invention.

The compounds of formula (V) can be prepared according to the process indicated in the experimental part. The experimental part can be illustrated as follows.

PREPARATION 1
4,7-Dihydroxy-8-methyl-3-(phenylazo)-2H-1-benzopyran-2-one
Stage A: $C_6H_5$ $N^+\equiv N,Cl^-$
30.86 ml of aniline is introduced at 10° C. into 138 ml of a 36% solution of hydrochloric acid. A solution containing 23.32 g of sodium nitrite and 123 ml of water is added while maintaining the temperature between 0 and 5° C. A solution is obtained which is maintained at 5° C. for 45 minutes. A product is obtained which is used as it is below.
Stage B: 4,7-Dihydroxy-8-methyl-3-(phenylazo)-2H-1-benzopyran-2-one
33.75 g of 4,7-dihydro-8-methyl-2H-1-benzopyran-2-one is introduced into 1.1 l of ethanol. 138.3 g of sodium acetate is added followed by 150 ml of the product prepared in Stage A. The reaction mixture is maintained under agitation for 30 minutes and 460 ml of water is added. Agitation is maintained for 1 hour. The product obtained is rinsed with water or methyl cyanide and with ether. After drying and 87.34 g of sought product is obtained.

PREPARATION 2
Cyclic 2,3-Carbonate and 1-(2,2,2-Trichloroethanimidate) of 6-Deoxy-5-C-methyl-4-O-methyl-L-lyxo-hexopyranose
Stage A: 6-Deoxy-5-C-methyl-4-O-methyl-L-lyxo-hexopyranose Cyclic 2,3-Carbonate
50 g of 6-deoxy-5-C-methyl-4-O-methyl-L-lyxo-hexopyranose is introduced into 2 l of dichloro 1,2-ethane. 44.3 g of carbonyl diimidazole is added. The reaction medium is taken to reflux for 3 hours 30 minutes, then left to return to ambient temperature followed by concentration. 120 g of product is obtained which is chromatographed on silica, eluting with a methylene chloride/acetone mixture 9-1. 23.19 g of sought product is obtained in this way.
Stage B: Cyclic 2,3-Carbonate and 1-(2,2,2-Trichloro-ethanimidate) of 6-Deoxy-5-C-methyl-4-O-methyl-L-lyxo-hexopyranose
276 mg of caesium carbonate, 18.17 g of the product prepared in Stage A and 16 ml of trichloromethane cyanide are introduced into 250 ml of methylene chloride. The reaction mixture is maintained under agitation for 3 hours. 7 ml of trichloromethane cyanide is added. Agitation is maintained for 1 hour and the product obtained is brought to dryness eluting with a cyclohexane/ethyl acetate mixture (5-5). 27.01 g of sought product is obtained in this way.

EXAMPLE 1
Cyclopropyl-carbamic Acid 3'-Ester of N-[7-[(6-deoxy-5-C-methyl-4-O-methyl-.alpha.-L-lyxo-hexopyranosyl)oxy]-4-hydroxy-8-methyl-2-oxo-2H-1-benzopyran-3-yl]-cyclopropanamide
Stage A: 7-[(2,3-O-Carbonyl-6-deoxy-5-C-methyl-4-O-methyl-.alpha.-L-lyxo-hexopyranosyl)oxy]]-4-hydroxy-8-methyl-3-(phenylazo)-2H-1-benzopyran-2-one
36.7 g of the product of Preparation 1 and 25 g of the product of Preparation 2 are introduced into 500 ml of methylene chloride. 1.2 ml of $BF_3$, $Et_2O$ is added. Agitation is carried out for 20 hours at 20° C. 100 ml of water is added followed by agitation, filtering and decanting. The precipitate is washed with methylene chloride and decanted, the organic phases are washed with water, combined, dried and concentrated. 500 ml of ethyl ether is added. Agitation is carried out for 1 hour at 20° C. and for 15 minutes at 0° C. The reaction medium is separated, rinsed and washed with ethyl ether. 30 g of sought product is obtained in this way (71%).
Stage B: 3-Amino-7-[(2,3-O-carbonyl-6-deoxy-5-C-methyl-4-O-methyl-.alpha.-L-lyxo-hexopyranosyl)oxy]]-4-hydroxy-8-methyl-2H-1-benzopyran-2-one
30 ml of water, 1.8 g of sodium acetate and 1.7 g of dithionite are added to a suspension containing 1.5 g of the product of the previous stage and 15 ml of ethanol. The reaction medium is taken to reflux over 30 minutes, then maintained under reflux for 10 minutes. The reaction medium is filtered then brought to 20° C., then cooled down to 0° C. followed by separation, impasting in ethyl ether, separation and drying. The sought product is obtained in this way (858 mg).

Stage C: N-[7-[(2,3-O-Carbonyl-6-deoxy-5-C-methyl-4-O-methyl-.alpha.-L-lyxo-hexopyranosyl)oxy]]-4-hydroxy-8-methyl-2-oxo-2H-1-benzopyran-3-yl]-cyclopropanecarboxamide 20 ml of ethyl acetate is added to 1 g of the product of the previous stage. The reaction medium is triturated with a spatula. 250 mg of pyridine is added. 256 mg of cyclopropane carboxylic acid chloride is added. Agitation is carried out for 1 hour 30 minutes at 20° C. Dilution is carried out with 100 ml of ethyl acetate and 50 ml of water. The reaction medium is decanted, washed with sodium acid carbonate, with water and with hydrochloric acid followed by drying, filtering and concentration. The product obtained is chromatographed on silica eluting with a hexane/ethyl acetate mixture (1-1). The sought product is obtained in this way.

Stage D: Cyclopropyl-carbamic Acid 3'-Ester of N-[7-[(6-Deoxy-5-C-methyl-4-O-methyl-.alpha.-L-lyxo-hexopyranosyl) oxy]-4-hydroxy-8-methyl-2-oxo-2H-1-benzopyran-3-yl]-cyclopropanamide 82 $\mu$l of cyclopropylamine and 283 $\mu$l of 1,8-diazabicyclo[5,4,0]undec-7-ene are added to a solution containing 453 mg of product of the previous stage and 10 ml of DMF. Agitation is carried out for 20 hours at 20° C. A dilute solution of monosodium phosphate is poured in. Extraction is carried out with ethyl acetate followed by washing with water, drying, filtering and concentration. 563 mg of product is obtained which is chromatographed eluting with a heptane/ethyl acetate mixture 30-70. Elution is carried out with methanol, 312 mg of product is obtained which is impasted in an ethyl acetate/methanol mixture 8-2. Separation is carried out, followed by concentration and 113 mg of sought product is obtained. Rf=0.18 heptane/ethyl acetate 30-70.

EXAMPLE 2

(1-Methylethoxy)-carbamic Acid 3'-Ester of N-[7-[(6-Deoxy-5-C-methyl-4-O-methyl-.alpha.-L-lyxo-hexopyranosyl) oxy]-4-hydroxy-8-methyl-2-oxo-2H-1-benzopyran-3-yl]-cyclopropane-carboxamide 102 mg of sodium hydride is added to a suspension containing 237 mg of isopyloxyamine hydrochloride and 7.5 ml of DMF. Agitation is carried out for 1 hour at 20° C. 0.25 ml of triethylamine and the product prepared in Stage C of Example 1 are added. The reaction medium is heated at 50° C. for 3 hours, 150 mg of DMAP is added and the temperature is maintained at 50° C. overnight. 150 mg of DMAP and 132 mg of isopyloxyamine hydrochloride are added.

Agitation is carried out for 20 hours at 50° C. The reaction medium is brought to 20° C. then poured into a normal solution of ice-cooled hydrochloric acid followed by extraction with ethyl acetate, washing with water, drying, filtering and concentration. 253 mg of product is obtained which is chromatographed on silica eluting with a heptane/ethyl acetate mixture 3-7. 48 mg of sought product is obtained, rf=0.15.

EXAMPLE 3

(2-Propynyloxy)-carbamic Acid 3'-Ester of N-[7-[(6-Deoxy-5-C-methyl-4-O-methyl-.alpha.-L-lyxo-hexopyranosyl) oxy]-4-hydroxy-8-methyl-2-oxo-2H-1-benzopyran-3-yl]-cyclopropane-carboxamide 1.0 ml of a 3 molar solution of $LiClO_4$ in $Et_2O$ is added to a suspension containing 302 mg of the product prepared in Stage C of Example 1 and 5 ml of ethyl ether. The mixture is triturated then placed under ultrasound for 15 minutes. Agitation is maintained for 5 hours, 15 ml of a solution of $LiClO_4/Et_2O$ is added. The reaction medium is agitated for 16 hours at 20° C., diluted with ethyl acetate and washed with water, followed by drying, filtering and concentration. 365 mg of product is obtained which is chromatographed on silica eluting with hexane/ethyl acetate (4-6) then with a methanol/ethyl acetate mixture 40-60. 36 mg of sought product is obtained.

By operating as previously, the following products were obtained:

(1-methylethoxy)-carbamic acid 3'-ester of N-[7-[(6-deoxy-5-C-methyl-4-O-methyl-.alpha.-L-lyxo-hexopyranosyl)oxy]-4-hydroxy-8-methyl-2-oxo-2H-1-benzopyran-3-yl]-benzeneacetamide ethoxy-carbamic acid 3'-ester of N-[7-[(6-deoxy-5-C-methyl-4-O-methyl-.alpha.-L-lyxo-hexopyranosyl) oxy]-4-hydroxy-8-methyl-2-oxo-2H-1-benzopyran-3-yl]-benzeneacetamide (1R-trans) ethoxy-carbamic acid 3'-ester of N-[7-[(6-deoxy-5-C-methyl-4-O-methyl-.alpha.-L-lyxo-hexopyranosyl) oxy]-4-hydroxy-8-methyl-2-oxo-2H-1-benzopyran-3-yl]-2,2-dimethyl-3-ethenyl-cyclopropanamide cyclopropyl-carbamic acid 3'-ester of N-[7-[(6-deoxy-5-C-methyl-4-O-methyl-.alpha.-L-lyxo-hexopyranosyl) oxy]-4-hydroxy-8-methyl-2-oxo-2H-1-benzopyran-3-yl]-benzeneacetamide cyclopropyl-carbamic acid 3'-ester of N-[7-[(6-deoxy-5-C-methyl-4-O-methyl-.alpha.-L-lyxo-hexopyranosyl) oxy]-4-hydroxy-8-methyl-2-oxo-2H-1-benzopyran-3-yl]-benzenepropanamide (1-methylethoxy)-carbamic acid 3'-ester of N-[7-[(6-deoxy-5-C-methyl-4-O-methyl-.alpha.-L-lyxo-hexopyranosyl) oxy]-4-hydroxy-8-methyl-2-oxo-2H-1-benzopyran-3-yl]-benzenepropanamide butoxy-carbamic acid 3'-ester of N-[7-[(6-deoxy-5-C-methyl-4-O-methyl-.alpha.-L-lyxo-hexopyranosyl) oxy]-4-hydroxy-8-methyl-2-oxo-2H-1-benzopyran-3-yl]-2-methyl-propanamide propoxy-carbamic acid 3'-ester of N-[7-[(6-deoxy-5-C-methyl-4-O-methyl-.alpha.-L-lyxo-hexopyranosyl) oxy]-4-hydroxy-8-methyl-2-oxo-2H-1-benzopyran-3-yl]-2-methyl-propanamide cyclopropyl-carbamic acid 3'-ester of N-[7-[(6-deoxy-5-C-methyl-4-O-methyl-.alpha.-L-lyxo-hexopyranosyl) oxy]-4-hydroxy-8-methyl-2-oxo-2H-1-benzopyran-3-yl]-cyclobutanamide.

PREPARATION 3

3-Amino-7-[[6-deoxy-5-C-methyl-4-O-methyl-3-O-[[(2-propynyloxy)amino]carbonyl]-2-O-[(tetrahydro-2H-pyran-2-yl)oxy]-.alpha.-L-lyxo-hexopyranosyl]oxy]-4-hydroxy-8-methyl-2H-1-benzopyran-2-one Stage A: 7-[[6-Deoxy-5-C-methyl-4-O-methyl-2-O-[(tetrahydro-2H-pyran-2-yl)oxy]-3-O[(triethylsily)oxy]-.alpha.-L-lyxo-hexopyrano-syl]oxy]-4-hydroxy-8-methyl-2H-1-benzopyran-2-one 28.0 g of product P prepared hereafter is subjected to hydrogenation under reduced pressure in the presence of palladium on carbon. The palladium is filtered off and rinsing is carried out with THF then concentrated under reduced pressure. 32.48 g of product is obtained which is purified on silica eluting with a hexane/ethyl acetate mixture 6-4.

Stage B: 7-[[6-Deoxy-5-C-methyl-4-O-methyl-2-O-[(tetrahydro-2H-pyran-2-yl)oxy]-3-O[(triethylsily)oxy]-.alpha.-L-lyxo-hexopyrano-syl]oxy]-4-hydroxy-8-methyl-3-(phenylazo)2H-1-benzopyran-2-one 3.54 g of aniline is added to 143 ml of a normal solution of hydrochloric acid at 0° C.,. Agitation is maintained for 15 minutes at 0° C. and a solution of 2.9 g of sodium nitrite in 30 cm$^3$ of water is added. A solution of 14.39 g of sodium acetate in 150 ml of water is added. Agitation is maintained for 15 minutes, then a solution containing the product of the previous stage in 150 ml of ethanol is added. Agitation is maintained for 15 minutes at 0° C., and 300 ml of AcOEt is added. The reaction medium is decanted, washed with sodium acid phosphate, dried and concentrated. 34 g of product is obtained which is purified by chromatography on silica eluting with hexane, then with a hexane/ethyl acetate mixture 60-40. 17.55 g of product is obtained.

Stage C: 7-[[6-Deoxy-5-C-methyl-4-O-methyl-2-O-[(tetrahydro-2H-pyran-2-yl)oxy]-.alpha.-L-lyxo-hexopyranosyl]oxy]-4-hydroxy-8 Methyl-3-(phenylazo)-2H-1-benzopyran-2-one 57.5 ml of a molar solution of Bu$_4$NF in THF is added to a solution containing the product prepared in the previous stage in 400 ml of THF. Agitation is maintained for 5 hours at 0° C. The reaction medium is washed with a saturated solution of NaH$_2$PO$_4$, decanted, concentrated and dried. 34 g of product is obtained which is purified by chromatography on silica eluting with hexane 60 AcOEt 40. 17.55 g of sought product is obtained.

Stage D: 7-[[6-Deoxy-5-C-methyl-4-O-methyl-3-O-[[(2-propynyloxy)-amino]carbonyl]-2-O-[(tetrahydro-2H-pyran-2-yl)oxy]-.alpha.-L-lyxo-hexopyranosyl]oxy]-4-hydroxy-8 methyl-3-(phenylazo)-2H-1-benzopyran-2-one a) 17.55 g of the product of the previous stage is solubilized at 0° C. in 250 ml of methylene chloride. 9.62 g of DMAP and 9 g of paranitrophenol chloroformate are added. Agitation is carried out for 1 hour and 1.40 g of paranitrophenol chloroformate is added. The reaction medium is concentrated under reduced pressure.

b) In a second flask under nitrogen at 0° C., propargyloxylamine hydrochloride is suspended in 250 ml DMF. 6.7 g of sodium hydride is added. The reaction mixture is maintained under agitation for 1 hour, then the product prepared in Stage a) to which the previous solution is added is taken up in 250 ml of DMF at 0° C. The reaction medium is maintained under agitation for 1 hour, then poured into a mixture of an aqueous solution of sodium acid phosphate and ethyl ether, followed by filtering, washing with ether and drying. 16.06 g of sought product is obtained.

Stage E: 3-Amino-7-[[6-deoxy-5-C-methyl-4-O-methyl-3-O-[[(2-propynyl-oxy)-amino]carbonyl]-2-O-[(tetrahydro-2H-pyran-2-yl)oxy]-.alpha.-L-lyxo-hexopyranosyl]oxy]-4-hydroxy-8 Methyl-2H-1-benzopyran-2-one A suspension containing 16 g of the product of the previous stage, 22.7 g of sodium dithionite, 10.7 g of sodium acetate, 400 ml of water and 90 ml of ethyl alcohol is immersed in an oil bath at 85° C. The reaction medium is maintained under agitation for 60 minutes, then filtered. The filtrate is kept in an ice bath for 2 hours, followed by separation and the crystals obtained are washed with water. After drying, 10.26 g of sought product is obtained.

PRODUCT P

7-[[6-Deoxy-5-C-methyl-4-O-methyl-2-O-(tetrahydro-2H-pyran-2-yl)-3-O-(triethylsilyl)-.alpha.-L-lyxo-hexopyranosyl]oxy]-4-(diphenylmethoxy)-8-methyl-2H-1-benzopyran-2-one Stage A: 4-(Diphenylmethoxy)-8-methyl-7-(tetrahydro-2H-pyran-2-yl)-2H-1-benzopyran-2-one 55 g of 4-hydroxy-8-methyl-7-(tetrahydro-2H-pyran-2-yl)-2H-1-benzopyran-2-one is introduced into 250 ml of anhydrous dimethylformamide heated to 40° C., and a solution of 58.3 g of diphenyldiazomethane in 250 ml of DMF is added dropwise. The addition is made over 3 hours while maintaining the temperature at 40° C. Several portions of 3 g of diphenyldiazomethane are again added and agitation is carried out for one hour at 40° C. The reaction medium is poured into 2 l of sulphuric ether. The organic solution is washed with an aqueous solution of sodium bicarbonate, with a solution of soda (0.1 M), with water and with salt water followed by evaporating to dryness. The residue is agitated in an isopropyl ether-hexane mixture (1–2) followed by separation and drying of the insoluble part. 20.5 g of sought product is obtained.

TLC CH$_2$Cl$_2$-AcOEt (95-5). Rf=0.44

Stage B: 4-(Diphenylmethoxy)-7-hydroxy-8-methyl-2H-1-benzopyran-2-one 35 ml of a 0.9 M solution of hydrochloric acid in methanol is added to a solution containing a mixture of 20 g of the product of Stage A, 100 ml of dichloromethane and 100 ml of methanol. Agitation is carried out for 2 hours at ambient temperature and the solvents are evaporated off. The residue is dispersed in absolute ethanol cooled down to 0° C. The insoluble part is separated followed by rinsing with ice-cooled alcohol then with sulphuric ether, and drying. 15.53 g of product is collected which is dispersed in ether, separated and dried. 14.54 g of sought product is obtained.

NMR $^1$H MHz, CDCl$_3$, ppm) δ 2.31 (s, 3H), 5.62 (s, 1H), 6.35 (s, 1H), 6.78 (d, 1H, J=_Hz), 7.75 (d, 1H, J=_Hz), 6.99 to 7.10 (m, _H), 7.30 to 7.42 (m, _H).

Stage C: 7-[[6-Deoxy-5-C-methyl-4-O-methyl-.alpha.-L-lyxo-hexopyranosyl]oxy]-4-(diphenylmethoxy)-8-methyl-2H-1-benzopyran-2-one A mixture of 91.13 g of the product of Stage B, 58.6 g of 6-deoxy-5-C-methyl-4-O-methyl-L-lyxo-hexopyranose and 80 g of triphenylphosphine in 900 ml of dichloromethane is cooled down to 0° C. 60 ml of diisopropylazodicarboxylate is added dropwise. Agitation is carried out for 1 hour at ambient temperature. 34 g of triphenylphosphine and 25 ml of diisopropylazodicarboxylate are added. Agitation is carried out for 1 hour at ambient temperature. 34 g of triphenylphosphine and 25 ml of diisopropylazodicarboxylate are added and agitation is carried out for 12 hours at ambient temperature. The reaction medium is concentrated under vacuum then chromatographed eluting with a toluene/isopropyl alcohol mixture (95-5). After combining the fractions, evaporating the solvents, and recrystallization from isopropyl ether, 86.33 g of sought product is obtained.

NMR $^1$H (300 MHz, CDCl$_3$, ppm) δ 1.13 (s, 3H), 1.37 (s, 3H), 2.24 (s, 3H), 2.69 (s, 1H), 2.79 (s, 1H), 3.38 (d, 1H, J=10 Hz), 3.60 (s, 3H), 4.24 (m, 1H), 4.28 (m, 1H), 5.56 (s, 1H), 5.64 (d, 1H, J=1.5 Hz), 6, (s, 1H), 7.18 (d, 1H), 7.81 (d, 1H), 7.39 (m, 10H).

Stage D: 7-[[6-Deoxy-5-C-methyl-4-O-methyl-3-O-(triethylsilyl)-alpha-L-lyxo-hexopyranosylloxy]-4-(diphenylmethoxy)-8-methyl-2H-1-benzopyran-2-one 26.6 g of imidazole and 70.15 ml of diisopropylethylamine are added to a solution cooled down to 0° C., containing 80 g of the product of the previous stage and 600 ml of dichloromethane. 33.5 ml of triethylsilyl chloride is added dropwise. Agitation is carried out for 1 hour at ambient temperature. The reaction medium is washed with an aqueous solution of sodium dihydrogen phosphate, 1 M, with water and with salt water, dried over magnesium sulphate, filtered and concentrated. 98.58 g of product is collected which is purified by chromatography on silica eluting with a dichloromethane acetone mixture (0.8 to 1%). 46.5 g of product is obtained.

NMR $^1$H (300 MHz, CDCl$_3$-d6, ppm) δ 0.60 (q, _H, J=_Hz), 0.74 (q, _H, J=_Hz), 0.97 (t, _H, J=_Hz), 1.00 (t, _H, J=_Hz), 1.10 (s, 3H), 1.32 (s, 3H), 2.24 (s, 2H), 2.74 (s, 1H), 3.31 (d, 1H, J=_Hz), 3.54 (s, 3H), 4.07 (m, 1H), 4.29 (dd, 1H, J=Hz), 5.50 (s, 1H), 5.65 (d, 1H, J=Hz), 6.35 (s, 1H), 7.28 (d, 1H, J=Hz), 7.81 (d, 1H, J=Hz), 7.40(m).

Stage E: 7-[[6-Deoxy-5-C-methyl-4-O-methyl-2-O-(tetrahydro-2H-pyran-2-yl)-3-O-(triethylsilyl)-alpha-L-lyxo-hexopyranosyl]oxy]-4-(diphenylmethoxy)-8-methyl-2H-1-benzopyran-2-one 19 ml of dihydropyrane and 400 mg of PTSA are added to a solution containing 67 g of the product of the previous stage and 1 l of dichloromethane. Agitation is carried out for 40 minutes at ambient temperature, 300 mg of PTSA is added. After 30 minutes, 100 mg of PTSA is added, then another 100 mg of PTSA. Agitation is carried out for a further 20 minutes, then finely ground sodium hydrogen carbonate is introduced. Agitation is carried out for 10 minutes, the reaction medium is diluted with a hexane/ethyl acetate mixture (1-2), washed with water and with salt water then dried followed by filtration and evaporation of the solvents. The product obtained was chromatographed eluting with a heptane/ethyl acetate mixture (4-1). 77.9 g of sought product is collected.

NMR $_1$H (300 MHz, DMSO-d$_6$, ppm) δ 0.64 (q, _H, J=Hz), 0.73 (q, _H, J=_Hz), 0.95 to 1.32 (_H), 2.25 (s, _H), 2.27 (s, _H), 3.30 (d, _H, J=Hz), 3.4 (d, _H, J=Hz), 3.50 (m, 2H), 3.93 (m, 2H), 3.53 (s, _H), 3.54 (s, _H), 4.04 to 4.15, 4.36 (dd, _H, J=_Hz), 4.94 (1), 4.96 (b), 5.50 (bs, H), 5.65 (bs), 6.37 (s, 1H), 7.15 (d, _H, J=_Hz), 7.19 (d, _HH, J=Hz), 7.81 (m, 1H), 7.30 to 7.44, 1.47 to 2.00.

EXAMPLE 4

(2-Propynyloxy)-carbamic Acid 3'-Ester of N-[7-[(6-Deoxy-5-C-methyl-4-O-methyl-.alpha.-L-lyxo-hexopyranosyl) oxy]-4-hydroxy-8-methyl-2-oxo-2H-1-benzopyran-3-yl]-benzamide 60 μl of triethylamine and 50 μl of benzyl chloride are added to a solution containing 200 mg of the product of Preparation 3 and 4 ml of methylene chloride. Agitation is carried out for 1 hour 30 minutes at 0° C. The temperature is allowed to rise to 20° C. The reaction medium is poured into a mixture of ice and monosodium phosphate followed by extraction with methylene chloride, drying, filtration and concentration. 400 ml of methanol is added at 20° C., 40 mg of TsOH, H$_2$O is added. Agitation is carried out for 2 hours at 20° C., followed by diluting with methylene chloride, washing with water, drying, filtering and concentration. 90 mg of product is obtained. The aqueous phase is extracted with ethyl acetate, followed by drying, filtering and concentration. 75 mg of product is obtained. The 90 mg and 75 mg of product are combined. Chromatography is carried out on silica eluting with methylene chloride, ethyl acetate, acetic acid 80-20-1. 105 mg of sought product is obtained.

EXAMPLE 5

(2-Propynyloxy)-carbamic Acid 3'-Ester of 7-[(6-Deoxy-6-C-methyl-4-O-methyl-.alpha.-L-mannopyranosyl) oxy]-4-hydroxy-3-[1-(methoxyimino)ethyl]8-methyl-2H-1-benzopyran-3-yl]-2-one 139 mg of 2-methoxyiminopropanoic acid and 250 mg of pentafluorophenol are solubilized at 20° C. in 10 ml of methylene chloride. 270 mg of DCC in solution in 10 ml of methylene chloride is added. Agitation is carried out for 2 hours 30 minutes at 20° C. followed by filtration. The filtrate is concentrated then redissolved in 10 ml of DMF. 5 ml of the solution obtained in this way is agitated at 20° C. under a nitrogen atmosphere and 250 mg of the product of Preparation 3 is added. Agitation is carried out for 16 hours at 20° C., followed by diluting with methylene chloride, washing with water, drying, filtering and concentration. The residue obtained is dissolved in 5 ml of methanol at 20° C. 80 mg of TsOH, 1H$_2$O is added. Agitation is carried out for 5 hours at 20° C. The reaction medium is purified by chromatography on silica eluting with a methylene chloride, ethyl acetate, acetic acid mixture 80-20-1 then hexane ethyl acetate 50-50. 100 mg of sought product is obtained, rf=0.1.

EXAMPLE 6

N-[7-[[6-Deoxy-5-C-methyl-4-O-methyl-3-O-[[(2-propynyloxy) Amino]carbonyl]-.alpha.-L-lyxo-hexopyranosyl]oxy]-4-hydroxy-8 methyl-2-oxo-2H-1-benzopyran-3-yl]-2-(2-pyridinylmethoxy)-acetamide Stage A: Ethyl 2-[(2-Pyridinyl)methoxy]-acetate 0.530 g of sodium hydride is added over 20 minutes at 0° C. to a solution of 1 g of 2-hydroxymethylpyridine and DMF. 1.6 ml of chloroethyl acetate is added at 0° C. 2 ml of a solution of sodium acid phosphate is poured in, then the reaction medium is concentrated under reduced pressure. The product obtained is chromatographed on silica eluting with a methylene chloride methanol mixture 90-10. 4.5 g of product is obtained which is chromatographed on silica eluting with a methylene chloride, methanol mixture 90-10. The product is obtained is purified and 1.30 g of sought product is obtained.

Stage B: 2-[(Pyridinyl)methoxy]acetic Acid 3.7 ml of a 2 N soda solution is added to a solution containing 1.3 g of the product prepared in the previous stage and 10 ml of ethanol. Agitation is maintained for 1 hour, the reaction medium is adjusted to pH <7 by adding a normal solution of hydrochloric acid, followed by concentrating under reduced pressure, taking up in acetone and filtering. The mother liquors are concentrated and 1.01 g of sought product is obtained.

Stage C: N-[7-[[6-Deoxy-5-C-methyl-4-O-methyl-3-O-[[(2-propynyloxy) Amino]carbonyl]-.alpha.-L-lyxo-hexopyranosyl]oxy]-4-hydroxy-8 Methyl-2-oxo-2H-1-benzopyran-3-yl]-2-(2-pyridinylmethoxy)-acetamide 0.2 g of the product of Preparation 3, 0.065 g of the product of Stage B, 0.053 g of HOBT and 0.075 g of EDCS and 6 ml of methylene chloride are maintained under agitation for 30 minutes. After concentrating to dryness, a product is obtained which is chromatographed on silica eluting with methylene chloride methanol 90-10. 148 mg of product is obtained which is taken up in methanol, 40 mg of PTSA is added. The product obtained is chromatographed eluting with a methylene chloride-methanol mixture 90-10. 0.110 g of sought product is obtained.

EXAMPLE 7

(2-Propynyloxy)-carbamic Acid 3'-Ester of N-[7-[(6-Deoxy-5-C-methyl-4-O-methyl-.alpha.-L-lyxo-hexopyranosyl) oxy]-4-hydroxy-8-methyl-2-oxo-2H-1-benzopyran-3-yl]-2-[(1,2,5-thiadiazol-3-yl)oxy]-acetamide Stage A: 2-[1,2,5-Thiadiazol-3-yl)oxy]-acetic Acid 5.93 ml of a 2 N solution of soda is added to a solution containing 1 g of ethyl ester of 2-[1,2,5-thiadiazol-3-yl) oxy]-acetic acid and 5 ml of ethanol. Agitation is maintained for 2 hours. The reaction medium is adjusted to pH 5–6 by adding a normal solution of hydrochloric acid then concentrated, and 1.054 g of product is obtained. Chromatography is carried out on silica eluting with a methylene chloride methanol mixture 90-10.

Stage B: (2-Propynyloxy)-carbamic Acid 3'-Ester of N-[7-[(6-Deoxy-5-C-methyl-4-O-methyl-.alpha.-L-lyxo-hexopyranosyl) oxy]-4-hydroxy-8-methyl-2-oxo-2H-1-benzopyran-3-yl]-2-[(1,2,5-thiadiazol-3-yl)oxy]-acetamide 0.105 g of the product of the previous stage is poured at 0° C. into 10 ml of methylene chloride. 2 drops of DMF are added and 0.126 ml of oxalyl chloride is added. The reaction medium is maintained under agitation for 30 minutes, concentrated under reduced pressure and taken up in methylene chloride. 0.164 ml of pyridine and 0.200 g of the product of Preparation 3 in 10 ml of methylene chloride are added. Agitation is maintained for 20 minutes. The reaction medium is poured into an ice-cooled solution of sodium chloride followed by extraction with methylene chloride and drying. A product is obtained which is chromatographed on silica eluting with a methylene chloride methanol mixture 90-10. 76 mg of product is obtained which is taken up in 4 ml of methanol. 22 mg of PTSA is added and agitation is maintained for 30 minutes followed by concentration under reduced pressure. The product obtained is purified by chromatography on silica eluting with a methylene chloride, methanol mixture 95-5. 30 mg of sought product is obtained.

By operating as above, the following products were obtained:

(2-propynyloxy)-carbamic acid 3'-ester of N-[7-[(6-deoxy-5-C-methyl-4-O-methyl-.alpha.-L-lyxo-hexopyranosyl)oxy]-4-hydroxy-8-methyl-2-oxo-2H-1-benzopyran-3-yl]-2-[(5-methyl-isothiazol-3-yl)oxy]-acetamide (2-propynyloxy)-carbamic acid 3'-ester of N-[7-[(6-deoxy-5-C-methyl-4-O-methyl-.alpha.-L-lyxo-hexopyranosyl)oxy]-4-hydroxy-8-methyl-2-oxo-2H-1-benzopyran-3-yl]-2-[[2'-ethyl-[2,5'-bithiazol]-4-yl)methoxy]-acetamide (2-propynyloxy)-carbamic acid 3'-ester of N-[7-[(6-deoxy-oxy]-4-hydroxy-8-methyl-2-oxo-2H-1-benzopyran-3-yl]-2-[(1-oxydo-2-pyridinyl)methoxy]-acetamide (trans)-(2-propynyloxy)-carbamic acid 3'-ester of N-[7-[(6-deoxy-5-C-methyl-4-O-methyl-.alpha.-L-lyxo-hexopyranosyl)oxy]-4-hydroxy-8-methyl-2-oxo-2H-1-benzopyran-3-yl]-2,2-dimethyl-3-(2-methylpropyl)-cyclopropanecarboxamide (1R-trans)(2-propynyloxy)-carbamic acid 3'-ester of N-[7-[(6-deoxy-5-C-methyl-4-O-methyl-.alpha.-L-lyxo-hexopyranosyl)oxy]-4-hydroxy-8-methyl-2-oxo-2H-1-benzopyran-3-yl]-2,2-dimethyl-3-ethyl-cyclopropanecarboxamide (2-propynyloxy)-carbamic acid 3'-ester of N-[7-[(6-deoxy-5-C-methyl-4-O-methyl-.alpha.-L-lyxo-hexopyranosyl)oxy]-4-hydroxy-8-methyl-2-oxo-2H-1-benzopyran-3-yl]-2-phenoxy-acetamide (2-propynyloxy)-carbamic acid 3'-ester of N-[7-[(6-deoxy-5-C-methyl-4-O-methyl-.alpha.-L-lyxo-hexopyranosyl)oxy]-4-hydroxy-8-methyl-2-oxo-2H-1-benzopyran-3-yl]-benzamide (2-propynyloxy)-carbamic acid 3'-ester of N-[7-[(6-deoxy-5-C-methyl-4-O-methyl-.alpha.-L-lyxo-hexopyranosyl)oxy]-4-hydroxy-8-methyl-2-oxo-2H-1-benzopyran-3-yl]-2-propyl-cyclopropanecarboxamide trans-(2-propynyloxy)-carbamic acid 3'-ester of N-[7-[(6-deoxy-5-C-methyl-4-O-methyl-.alpha.-L-lyxo-hexopyranosyl)oxy]-4-hydroxy-8-methyl-2-oxo-2H-1-benzopyran-3-yl]-2-(methoxymethyl)-cyclopropanecarboxamide trans-(2-propynyloxy)-carbamic acid 3'-ester of 2-(butoxymethyl)-N-[7-[(6-deoxy-5-C-methyl-4-O-methyl-.alpha.L-lyxo-hexopyranosyl)oxy]-4-hydroxy-8-methyl-2-oxo-2H-1-benzopyran-3-yl]-cyclopropanecarboxamide (2-propynyloxy)-carbamic acid 3'-ester of N-[7-[(6-deoxy-5-C-methyl-4-O-methyl-.alpha.L-lyxo-hexopyranosyl)oxy]-4-hydroxy-8-methyl-2-oxo-2H-1-benzopyran-3-yl]-benzene-acetamide (2-propynyloxy)-carbamic acid 3'-ester of N-[7-[(6-deoxy-5-C-methyl-4-O-methyl-.alpha.L-lyxo-hexopyranosyl)oxy]-4-hydroxy-8-methyl-2-oxo-2H-1-benzopyran-3-yl]-2-(1-hydroxy-Propyl)-cyclopropanecarboxamide (2-propynyloxy)-carbamic acid 3'-ester of N-[7-[(6-deoxy-5-C-methyl-4-O-methyl-.alpha.L-lyxo-hexopyranosyl)oxy]-4-hydroxy-8-methyl-2-oxo-2H-1-benzopyran-3-yl]-2-[(phenyl-methoxy)methyl]-cyclopropanecarboxamide (2-propynyloxy)-carbamic acid 3'-ester of N-[7-[(6-deoxy-5-C-methyl-4-O-methyl-.alpha.L-lyxo-hexopyra-nosyl)oxy]-4-hydroxy-8-methyl-2-oxo-2H-1-benzopyran-3-yl]-4-pyridinecarboxamide 1-oxide (2-propynyloxy)-carbamic acid 3'-ester of N-[7-[(6-deoxy-5-C-methyl-4-O-methyl-.alpha.L-lyxo-hexopyra-nosyl)oxy]-4-hydroxy-8-methyl-2-oxo-2H-1-benzopyran-3-yl]-3-pyridinecarboxamide 1-oxide 2-propenyl 7-[[6-deoxy-5-C-methyl-4-O-methyl-3-0[[(2-propynyloxy) amino]carbonyl]-.alpha.L-lyxo-hexopyranosyl]oxy]-4-hydroxy-8-methyl-2-oxo-2H-1-benzopyran-3-carbamate (2-propynyloxy)-carbamic 3'-ester acid of N [7-[(6-deoxy-5-C-methyl-4-O-methyl-.alpha.L-lyxo-hexopyranosyl)oxy]-4-hydroxy-8-methyl-2-oxo-2H-1-benzopyran-3-yl]-5-thiazolecar-boxamide N-[7-[[6-deoxy-5-C-methyl-4-O-methyl-3-O-[[(2-propynyloxy) amino]carbonyl]-.alpha.-L-lyxo-hexopyranosyl]oxy]-4-hydroxy-8-methyl-2-oxo-2H-1-benzopyran-3-yl]-alpha-(hydroxymethyl)-benzeneacetamide (isomer A)

N-[7-[[6-deoxy-5-C-methyl-4-O-methyl-3-O-[[(2-propynyloxy) amino]carbonyl]-.alpha.-L-lyxo-hexopyranosyl]oxy]-4-hydroxy-8-methyl-2-oxo-2H-1-benzopyran-3-yl]-alpha-(hydroxymethyl)-benzeneacetamide (isomer B)

N-[7-[[6-deoxy-5-C-methyl-4-O-methyl-.alpha.-L-lyxo-hexopyranosyl]oxy]-4-hydroxy-8-methyl-2-oxo-2H-1-benzopyran-3-yl]-4-methyl-1-piperazinecarboxamide N-[7-[[6-deoxy-5-C-methyl-4-O-methyl-3-O-[[(2-propynyloxy) amino]carbonyl]-.alpha.-L-lyxo-hexopyranosyl]oxy]-4-hydroxy-8-methyl-2-oxo-2H-1-benzopyran-3-yl]-3-hydroxy-2-phenoxy-propanamide (isomer A)

7-[[6-deoxy-5-C-methyl-4-O-methyl-3-O-[[(2-propynyloxy) amino]carbonyl]-.alpha.-L-lyxo-hexopyranosyl]oxy]-4-hydroxy-8-methyl-2-oxo-2H-1-benzopyran-3-yl]-3-hydroxy-2-phenoxy-propanamide (isomer B)

N-[7-[[6-deoxy-5-C-methyl-4-O-methyl-3-O-[[(2-propynyloxy) amino]carbonyl]-.alpha.-L-lyxo-hexopyranosyl]oxy]-4-hydroxy-8-methyl-2-oxo-2H-1-benzopyran-3-yl]-5-methyl-4-hexenamide N-[7-[[6-deoxy-5-C-methyl-4-O-methyl-3-O-[[(2-propynyloxy) amino]carbonyl]-.alpha.-L-lyxo-hexopyranosyl]oxy]-4-hydroxy-8-methyl-2-oxo-2H-1-benzopyran-3-yl]-2,2,2-trifluoro-acetamide PREPARATION 4
6-Deoxy-5-C-ethyl-6-C-methyl-4-O-methyl-2,3-O-(1-methyl ethylidene)-L-lyxohexopyranose Stage A: [4S-[4-.Alpha.,5-.alpha.(S*)]]-β,β-diethyl-2,2-dimethyl-5-(hydroxymethyl)-α-methoxy-1,3-dioxolan-4-ethanol 400 ml of 1 M ethyl magnesium bromide in solution in THF is introduced into 250 ml of tetrahydrofuran (THF), agitation is carried out for 15 minutes, then 25.2 g of .Delta.-lactone of 2-O-methyl-3,4-O-(1-methylethylidene)-L-arabinonic acid and 126 ml of THF are introduced. Agitation is carried out for 1 hour 30 minutes while allowing the reaction medium to return to ambient temperature. The reaction medium is poured onto 480 g of an ice-water mixture (1:1) and agitated for 15 minutes. The aqueous phase is decanted and 80 g of sodium chloride is added to it. The aqueous phase is reextracted with methylene chloride. The organic phases (THF+methylene chloride) are combined, dried over sodium sulphate, filtered then evaporated to dryness under vacuum in a bath at 50° C. After drying, 32.9 g of sought product is obtained.

Stage B: .Delta.-lactone of 5-C-Ethyl-6-C-methyl-4-O-methyl-2,3-O-(1-methylethylidene)-L-lyxonic Acid 450 ml of dimethylsulphoxide (DMSO), 246 ml of triethylamine (TEA) and 45.6 g of the product obtained according to Stage A are introduced into 450 ml of methylene chloride. 90 g of pyridine trioxide sulphide complex is added by portions while maintaining the temperature below 30° C. Agitation is continued for 2 hours 30 minutes. 500 ml of ether is then introduced then the reaction medium is poured onto 500 g of ice+water (1:1). After decanting, the aqueous phase is reextracted with 500 ml of ether. The organic phases are combined, dried over sodium sulphate, filtered then evaporated to dryness under vacuum. 66 g of product is obtained. Reextraction is carried out 3 times with 250 ml of ether and washed with 150 ml of water. The organic phases are again combined, dried over sodium sulphate, filtered then evaporated to dryness under vacuum. 39 g of sought product is obtained.

Stage C: 6-Deoxy-5-C-ethyl-6-C-methyl-4-O-methyl-2,3-O-(1-methyl Ethylidene)-L-lyxohexopyranose 39 g of the product of the previous stage is introduced into 390 ml of tetrahydrofuran (THF). The reaction medium is cooled down to 0° C., then 120 ml of a 1.5 M solution of DIBAH in toluene is introduced while maintaining the temperature at 0° C. Agitation is carried out for 1 hour 30 minutes while allowing the temperature to rise. 500 ml of a 1 M aqueous solution of sodium and potassium double tartrate is poured onto the reaction medium while maintaining the temperature below 20° C. Agitation is carried out for 1 hour at ambient temperature. After decanting, the aqueous phase is reextracted with methylene chloride. The organic phases are combined (THF +methylene chloride), dried over magnesium sulphate, filtered then evaporated to dryness. 38.46 g of sought product is obtained.

Stage D: 6-Deoxy-5-C-ethyl-6-C-methyl-4-O-methyl-L-lyxohexopyranose 67.7 g of the product of the previous stage, 183 ml of 0.1 N sulphuric acid are introduced into 183 ml of water. The reaction medium is heated to 70° C. for 2 hours 30 minutes then allowed to return to ambient temperature. Then barium carbonate is added in order to adjust the pH to approximately 7-8. The medium is filtered then rinsed with 60 ml of water. The filtrate is concentrated under vacuum at 45° C. The residue is taken up in 50 ml of ethyl acetate then evaporated to dryness under vacuum. The operation is repeated three times each time with 50 ml of AcOEt. The oil obtained is solubilized in 50 ml of methylene chloride. The reaction medium is again filtered. After evaporation of the methylene chloride, 55.87 g of product is obtained. The product is taken up in 80 ml of ether and agitated for 3 hours at ambient temperature, separated, rinsed with a minimum amount of ether then dried in an oven under vacuum at 45° C. 28.32 g of sought product is obtained. M.p.=100° C.

EXAMPLE 8
N-[7-[[6-Deoxy-5-C-ethyl-6-C-methyl-4-O-methyl-3-O-[(5-methyl-1H-pyrrol-5-yl)carbonyl)-.alpha.-L-lyxo-hexopyranosyl)oxy]-4-hydroxy-8-methyl-2-oxo-2H-1-benzopyran-3-yl]-2-methyl-propanamide Stage A: 6-Deoxy-5-C-ethyl-6-C-methyl-4-O-methyl-L-lyxohexopyranose Cyclic 2,3-carbonate A mixture of 3.083 g of 6-deoxy-5-C-ethyl-6-C-methyl-4-O-methyl-L-lyxohexopyranose and 50 ml of methylene chloride is cooled down to 0° C. 3.4 g of 1,1 carbonyldi-imidazole and 0.168 ml of 1,8-diazo-bicyclo[5-4-0]-undec-7-ene are added, followed by pouring on 30 ml of a 1M solution of sodium hydrogen phosphate and extraction with methylene chloride. The organic phases are washed with water, dried, filtered and concentrated. 4.09 g of crude sought product is obtained, which is used as it is in the following stage.

Stage B: 6-Deoxy-5-C-ethyl-6-C-methyl-4-O-methyl-L-lyxo-hexopyranoside Cyclic 2,3-carbonate and 1-(2,2,2-Trichloroethanimidate)

3.05 g of trichloroacetonitrile is added dropwise to a mixture of 78 mg of caesium carbonate, 20 ml of methylene chloride and 3.97 g of the product of Stage A. Agitation is carried out for 16 hours at ambient temperature followed by filtration and concentration. 5.29 g of sought product is obtained.

Stage C: 7-[(2,3-O-Carbonyl-6-deoxy-5-C-ethyl-6-C-methyl-4-O-methyl-.alpha.-L-lyxo-hexopyranosyl)oxy]-4-hydroxy-8-methyl-3-(phenylazo)-2H-1-benzopyran-2-one 0.13 ml of boron trifluoride etherate [$BF_3(OEt)_2$] is introduced into a mixture containing 90 ml of methylene chloride, 3.10 g of 4,7-dihydroxy-8-methyl-3-(phenylazo)-2H-1-benzopyran-2-one and 4.7 g of the product of the previous stage, followed by filtration and concentration. 7.05 g of a product is obtained which is purified by FLASH chromatography on silica eluting with a methylene chloride isopropanol mixture 95-5. A product is obtained which crystallizes from ether, followed by separation and drying under reduced pressure. 2.32 g of sought product is obtained in this way.

Stage D: 3-Amino-7-[(2,3-O-Carbonyl-6-deoxy-5-C-ethyl-6-C-methyl-4-O-methyl-.alpha.-L-lyxo-hexopyranosyl) oxy]-4-hydroxy-8-methyl-2H-1-benzopyran-2-one A mixture of 2.32 g of the product of Stage C, 200 ml of ethanol and 232 mg of 10% palladium on carbon is placed under hydrogen pressure (approximately 1400 mbar) for 2 hours. The reaction medium is filtered, washed with an ethanol methylene chloride mixture and concentrated with the rotary evaporator under reduced pressure. 1.54 g of product is obtained.

Stage E: N-[7-[(2,3-O-Carbonyl-6-deoxy-5-C-ethyl-6-C-methyl-4-O-methyl-.alpha.-L-lyxo-hexopyranosyl)oxy]-4-hydroxy-8-methyl-2-oxo-2H-1-benzopyran-3-yl]-2-methyl-propanamide 0.55 ml of pyridine and 0.4 ml of isobutyryl chloride are introduced dropwise into a mixture of 1.5 g of the product of the previous stage and 30 ml of methylene chloride. The reaction medium is maintained under agitation for one hour then poured into 20 ml of a 1 M solution of sodium hydrogen phosphate followed by extraction with methylene chloride. The organic phases are washed, dried, filtered and concentrated. 1.8 g of sought product is obtained.

Stage F: N-[7-[(6-Deoxy-5-C-ethyl-6-C-methyl-4-O-methyl-alpha.-L-lyxo-hexopyranosyl)oxy]-4-hydroxy-8-methyl-2-oxo-2H-1-benzopyran-3-yl]-2-methyl-propanamide A solution containing 303 mg of the product of the previous stage, 5 ml of methanol and 1.4 ml of a 0.5 N aqueous solution of sodium hydroxide is agitated for 2 hours. 50 ml of a 1 M aqueous solution of sodium hydrogen phosphate is poured in followed by extraction with methylene chloride, washing with water, drying, filtration and concentration. 270 mg of sought product is obtained.

Stage G: N-[7-[[6-Deoxy-5-C-ethyl-6-C-methyl-4-O-methyl-3-O-[(5-methyl-1H-pyrrol-5-yl)carbonyl]-.alpha.-L-lyxo-hexopyranosyl)oxy]-4-hydroxy-8-methyl-2-oxo-2H-1-benzopyran-3-yl]-2-methyl-propanamide 260 mg of the product of the previous stage, 4 ml of dimethylformamide, 0.168 ml of (1,8-diaza-bicyclo[5-4-O]-undec-7-ene) and 152 mg of 2-2-2-trichloroethyl 5-methyl 2-pyrrolcarboxylate are agitated for 4 hours at ambient temperature. The reaction medium is poured into 20 ml of a 1 M aqueous solution of sodium hydrogen phosphate, followed by extraction with ethyl acetate. The organic phases are combined, dried, filtered and concentrated. 260 mg of crude sought product is obtained which is purified by chromatography on silica eluting with a methylene chloride methanol mixture 95-5. 110 mg of this product is taken and 27 microlitres of 1,8-diaza-bicyclo[5,4,0]-undec-7-ene and 3 ml of methylene chloride are added. Agitation is carried out for 1 hour at ambient temperature, followed by pouring into 3 ml of a 1 M aqueous solution of sodium hydrogen phosphate. Extraction is carried out with methylene chloride. The organic phases are washed with water, combined and dried over magnesium sulphate, filtered and concentrated. 100 mg of sought product is obtained.

M.p.=140–142° C.

EXAMPLE 9

(2-Propynyloxy)-carbamic Acid 3'-Ester of N-[7-[(6-Deoxy-5-C-ethyl-6-C-methyl-4-O-methyl-.alpha.L-lyxo-hexopyranosyl)-oxy]-4-hydroxy-8-methyl-2-oxo-2H-1-benzopyran-3-yl]-2-methyl-propanamide 303 mg of the product prepared in the stage before last of the previous example, 3 ml of pyridine, 60 mg of lithium perchlorate and 610 mg of O-propargyl hydroxylamine hydrochloride are agitated for 50 hours at ambient temperature. The reaction medium is kept in a freezer for 3 days, agitated again for 4 hours then poured into 10 ml of water followed by extraction with methylene chloride. The organic phases are washed, dried over magnesium sulphate, filtered and concentrated. 420 mg of product is obtained which is purified by chromatography on silica (eluent methylene chloride-methanol 95-5). 170 mg of a 3/2 regioisomeric product is obtained in a 75-25 mixture.

PREPARATION 5

[7R-(7.Alpha.,8.beta.,9.beta.,10.alpha.)]-4-hydroxy)-7-[[10-methoxy-8-[(tetrahydro-2H-pyran-2-yl)oxy]-9-[(triethylsily)-oxy]-6-oxaspiro[4,5]decan-7-yl)oxy]-8-methyl-2H-1-benzopyran-2-one Stage A: [4S-[4.Alpha.,5.alpha.(S*)]]-2,2-Dimethyl-5-[(1-hydroxyclopentyl)methoxymethyl]-1,3-dioxolane-4-methanol 20 ml of a dibromobutane solution (106 ml of dibromobutane in 200 ml of THF) is introduced into a mixture containing 43 g of magnesium, 100 ml of THF and an iodine crystal. The reaction mixture is placed under ultrasound. 1.7 l of THF is added. The remainder of the dibrominated solution is added. Agitation is maintained for 2 hours 30 minutes. A solution containing 80.37 g of delta-lactone of 2-O-methyl-3,4-O-(1-methylethylidene)-L-arabinic acid and 1 litre of THF are added at 17° C. Agitation is carried out for 4.5 hours at ambient temperature. The reaction medium is cooled down to 0° C. and a saturated solution of ammonium chloride is added. After decanting, the organic phase is removed and extraction is carried out with a solution of ethyl acetate with 20% heptane, followed by washing, drying and evaporating to dryness. 111.85 g of sought product is obtained.

Stage B: [3'aS-(3'a.alpha.,7'.alpha,7'a.beta.)]-7'methoxydihydro-spiro [cyclopentane-1,6'-[6H]-1,3-dioxolo[4,5-c]pyran]-4'(3aH)-one 221 g of PySO3 is added to a solution containing 111 g of the product prepared in Stage A and a mixture of one litre of methylene chloride, 1 litre of DMSO, 0.607 l of triethylamine. Agitation is carried out for 2 hours at ambient temperature. The reaction medium is poured into an aqueous solution of sodium acid phosphate followed by extraction with an ethyl acetate, heptane mixture (1-1), drying, filtration and evaporation to dryness. 57.7 g of sought product is obtained.

Stage C: [8R-(8.Alpha.,9.alpha,10.beta)]-10-methoxy-6-oxaspiro[4,5]-decane-7,8,9-triol 157 ml of a 1.5 M solution of dibutylaluminium hydride in toluene is added at –5° C. to a solution containing 56 g of the product of the previous stage and 300 ml of THF. Agitation is carried out at –3° C. for 1 hour. 1 litre of a 1 M solution of sodium and potassium double tartrate is added. Agitation is carried out for 15 minutes at ambient temperature. The reaction medium is extracted with an ethyl acetate-heptane mixture 1-1, washed with water then with salt water, dried and evaporated to dryness. The residue obtained is agitated at 70° C. in the presence of 150 ml of a 0.1 N solution of sulphuric acid and 150 ml of water for 2.5 hours. The reaction medium is cooled down to ambient temperature followed by filtration and evaporation to dryness. 49 g of the sought product is obtained.

Stage D: [7R-(7.Alpha.,8.beta,9.beta.,10.alpha.)]-7-[(8,9-dihydroxy-10-methoxy-6-oxaspiro[4,5]-decan-7-yl)oxy]-4-(diphenylmethoxy)-8-methyl-2H-1-benzopyran-2-one 45.30 g of DIAD is added dropwise at 0° C. to a mixture of 49 g of the product of Preparation 3, 73 g of 4-(diphenylmethoxy)-7-hydroxy-8-methyl-2H-1-benzopyran-2-one prepared as indicated in Preparation 6 and 59 g of triphenylphosphine. Agitation is carried out for 1.5 hour at ambient temperature. 1 equivalent of triphenylphosphine and of DIAD are added at 0° C. The solvents are evaporated off followed by taking up in ether and the sought product is obtained.

Stage E: [7R-(7.Alpha.,8.beta.,9.beta.,10.alpha.)]-4-(diphenyl-methoxy)-7-[[8-hydroxy-10-methoxy-9-[(triethylsily)oxy]-6-oxaspiro[4,5]-decan-7-yl)oxy]-8-methyl-2H-1-benzopyran-2-one 15.21 g of triethylsilane chloride is added at 0° C. to a solution containing 48 g of the product of the previous stage and 400 ml of methylene chloride. The reaction medium is agitated for 1 hour at 0° C., washed with a 1 M solution of sodium acid phosphate, rinsed with water and dried. The product obtained is chromatographed on silica eluting with a methylene chloride acetone mixture 99-1 then with a toluene terbutylmethylether mixture. 28.37 g of the sought product is obtained.

Stage F: [7R-(7.Alpha.,8.beta.,9.beta.,10.alpha.)]-4-(diphenyl-methoxy)-7-[[10-methoxy-8-[(tetrahydro-2H-pyran-2-yl)oxy]-9- [(triethylsily)oxy]-6-oxaspiro[4,5]-decan-7-yl)oxy]-8-methyl-2H-1-benzopyran-2-one 7.57 ml of 2,3-dihydropyran and 400 mg of paratoluene sulphonic acid are added to a solution containing 28.1 g of the product of the previous stage and 250 ml of dichloromethane. Agitation is carried out for 1 hour at ambient temperature. Sodium Bicarbonate is added and the reaction medium is agitated for 20 minutes at ambient temperature and washed with water. The organic phases are dried over sodium sulphate. The product obtained is chromatographed on silica eluting with a heptane-ethyl acetate mixture 4,1. 16.81 g of sought product is obtained.

Stage G: [7R-(7.Alpha.,8.beta.,9.beta.,10.alpha.)]-4-hydroxy-7-[[10-methoxy-8-[(tetrahydro-2H-pyran-2-yl)oxy]-9-[(triethylsily)-oxy]-6-oxaspiro[4,5]-decan-7-yl)oxy]-8-methyl-2H-1-benzopyran-2-one A solution of 16.19 g of the product of the previous stage, 150 ml of THF, is agitated under hydrogen atmosphere in the presence of 810 mg of palladium on carbon. After filtration, 15.1 g of sought product is obtained.

PREPARATION 6

4-(Diphenylmethoxy)-7-hydroxy-8-methyl-2H-1-benzopyran-2-one

Stage A: 4-(Diphenylmethoxy)-8-methyl-7-(tetrahydro-2H-pyran-2-yl)-2H-1-benzopyran-2-one 55 g of 4-hydroxy-8-methyl-7-(tetrahydro-2H-pyran-2-yl)-2H-1-benzopyran-2-one is introduced into 250 ml of anhydrous dimethylformamide heated to 40° C., and a solution of 58.3 g of diphenyldiazomethane in 250 ml of DMF is added dropwise. The addition is made over 3 hours while maintaining the temperature at 40° C. Several portions of 3 g of diphenyldiazomethane are added again and agitation is carried out for one hour at 40° C. The reaction medium is poured into 2 l of sulphuric ether. The organic solution is washed with an aqueous solution of sodium bicarbonate, with a solution of soda (0.1 M), with water and with salt water followed by evaporation to dryness. The residue is agitated in an isopropyl ether-hexane mixture (1-2) followed by separation. The insoluble part is dried. 20.5 g of sought product is obtained.

TLC $CH_2Cl_2$-AcOET 59565°. Rf=0.44.

Stage B: 4-(Diphenylmethoxy)-7-hydroxy-8-methyl-2H-1-benzopyran-2-one 35 ml of a 0.9 M solution of hydrochloric acid in methanol is added to a solution containing a mixture of 20 g of the product of Stage A, 100 ml of dichloromethane and 100 ml of methanol. Agitation is carried out for 2 hours at ambient temperature and the solvents are evaporated off. The residue is dispersed in absolute ethanol cooled down to 0° C. The insoluble part is separated and rinsed with ice-cooled alcohol then with sulphuric ether. After drying, 15.53 g of product is collected which is dispersed in ether, separated and dried. 14.54 g of sought product is obtained.

NMR 1H(300 MHz, CDCl3, ppm) δ 2.31 (s, 3H), 5.62 (s, 1H), 6.35 (s, 1H), 6.78 (d, 1H, J=__Hz), 7.75 (d, 1H, J=__Hz), 6.99 to 7.10 (m, __H), 7.30 to 7.42 (m, __H).

EXAMPLE 10

[7R-(7.α.,8.β,9.β,10.α)]-(2-Propynyloxy)-carbamate of 8-Hydroxy-7-[4-hydroxy-8-methyl-2-oxo-3-(benzoylamino)-2H-1-benzopyran-7-yl)-10-methoxy-6-oxaspiro[4,5]decan-9-yl Stage A: [7R-(7.α.,8.β,9.β,10.α)]-4-Hydroxy-7-[[10-methoxy-9-[(triethylsilyl)oxy]-6-oxaspiro[4,5]decan-7-yl]oxy]-8-methyl-3-(phenylazo)-2H-1-benzopyran-2-one Aniline (1.44 ml) is added dropwise to an aqueous solution of hydrochloric acid (27 ml) cooled down to 0° C. This mixture is agitated at 0° C. for five minutes. An aqueous solution of sodium nitrite (1.18 g: in solution in 10 ml of water) is then introduced dropwise. After agitation for 20 minutes at 0° C., sodium acetate (8.41 g) is added and agitation is carried out for a further 10 minutes. Ethanol (30 ml) is then added. Still at 0° C., a solution of [7R-(7.α.,8.β,9.β,10.α)]-4-hydroxy-7-[[10-methoxy-8-[(tetrahydro-2H-pyran-2-yl)oxy]-9-[(triethylsilyl)oxy]-6-oxaspiro[4,5]decan-7-yl]oxy]-8-methyl-2H-1-benzopyran-2-one of Preparation 5, 13.15 mmoles in 30 ml of THF is introduced dropwise. This mixture is agitated for forty minutes at 0° C. The reaction solution is poured into an aqueous solution of sodium dihydrogen phosphate (1M: 100 ml). Extraction is carried out with an AcOEt-heptane mixture (1:1). The organic solution is washed with water then dried over sodium sulphate, filtered and concentrated to dryness. The sought product is collected in this way.

Stage B: [7R-(7.α.,8.β,9.β,10.α)]-7-[(8,9-Dihydro-10-methoxy-6-oxaspiro[4.5]decan-7-yl]oxy]-4-hydroxy-8-methyl-3-(phenylazo)-2H-1-benzopyran-2-one A solution of tetrabutylammonium fluoride (1M in THF; 20 ml) is added dropwise to a solution, cooled down to 0° C., of the previous product in anhydrous tetrahydrofuran (170 ml). The temperature is allowed to rise and agitation is carried out for 1 hour at ambient temperature. Tetrabutylammonium fluoride (1M in THF: 20 ml) is again added and agitation is carried out for a further hour. The reaction solution is poured into an aqueous solution of sodium dihydrogen phosphate (100 ml). Extraction is carried out with an AcOEt-heptane mixture (80-20). The organic solution is washed with water then dried over magnesium sulphate, filtered and concentrated to dryness. 9 g of crude product is collected which is purified by chromatography eluting with a dichloromethane-acetone mixture (94:6).

Stage C: [3'aR-(3'a.α.,4'α.,7'α.,7'a.α)]-4'-[[4-Dihydro-8-methyl-3-(phenylazo)-2H-1-benzopyran-7-yl]oxy]-7'-methoxy-tetrahydro-spiro[cyclopentane-1,6'[6H-1,3]dioxolo[4,5-c]pyran]-2'-one The mixture of the product of Stage B (2.42 g) and carbonyldiimidazole (1.6 g) in anhydrous tetrahydrofuran (30 ml) is heated to reflux. After forty five minutes, the cooled reaction mixture is poured into an aqueous solution of sodium hydrogen sulphate (10% sol.: 20 ml) then extraction is carried out with dichloromethane. The organic phase is dried over magnesium sulphate followed by filtration and evaporation to dryness. The residue is purified by chromatography on silica, eluting with a dichloromethane-acetone mixture (95-5). 2.35 g of the sought product is collected.

Stage D: [3'aR-(3'a.α.,4'α.,7'α.,7'a.α)]-4'-[[3-Amino-4-hydroxy-8-methyl-2-oxo-2H-1-benzopyran-7-yl]oxy]-7'-methoxy-tetrahydro-spiro[cyclopentane-1,6'[6H-1,3]dioxolo[4,5-c]pyran]-2'-one The solution of the product of the previous stage in tetrahydrofuran (30 ml) is vigorously agitated at ambient temperature, in the presence of Pd/C (0.250 G: 10%), under a hydrogen atmosphere. After forty minutes the reaction is complete. The catalyst is eliminated by filtration followed by evaporation to dryness. The residue is concretized in an ether-pentane mixture under ultrasound then isolated by filtration. After drying, 1.85 g of sought product is recovered.

Stage E: [3'aR-(3'a.α.,4'α.,7'α.,7'a.α.)]-N-[4-Hydroxy-7-[(7'-methoxy-2'-oxo-tetrahydro-spiro[cyclopentane-1,6' [6H-1,3]dioxolo[4,5-c]pyran]-4'-yl)oxy]-8-methyl-2-oxo-2H-1-benzopyran-3-yl]-benzamide Triethylamine (177 μl) is introduced dropwise to a suspension cooled down to 0° C. of the product of the previous stage in dichloromethane (5 ml). 134 μl of benzoyl chloride is added by syringe. The reaction solution is agitated for 1 hour at 0° C. Triethylamine (18 μl) and benzoyl chloride (13 μl) are again added and the reaction mixture is agitated for a further hour at 0° C. The reaction solution is poured into an aqueous solution of sodium dihydrogen-phosphate (1 M: 100 ml). Extraction is carried out with an AcOEt-heptane mixture (80:20). The organic solution is washed with water then dried over magnesium sulphate, filtered and concentrated to dryness. The residue is purified by chromatography eluting with a heptane-ethyl acetate mixture (2:1). 420 mg of sought product is obtained.

Stage F: [7R-(7.α.,8β.,9β.,10.α)]-(2-Propynyloxy)-carbamate of 8-Hydroxy-7-[4-hydroxy-8-methyl-2-oxo-3-(benzoylamino)-2H-1-benzopyran-7-yl]-10-methoxy-6-oxaspiro[4,5]decan-9-yl O-propargylhydroxyamine (822 mg) and lithium perchlorate (82 mg) are added successively to a solution of the product of the previous stage in pyridine (dried over potash; 4 ml). The reaction medium is agitated for 2.5 days at ambient temperature. The reaction solution is poured into an aqueous solution of sodium hydrogen sulphate (10%: 100 ml). Extraction is carried out with an AcOEt-heptane mixture (80–20). The organic solution is washed with water then dried over magnesium sulphate, filtered and concentrated to dryness. 497 mg of crude sought product is obtained which is chromatographed on silica eluting with a dichloromethane methanol mixture (94: 6). 263 mg of sought product is obtained.

EXAMPLE 11

[7R-(7.α.,8β.,9β.,10.α)]-(2-Propynyloxy)-carbamate of 7-[4-Hydroxy-8-methyl-3-[(2-methyl-1-oxo-propyl) amino]-2-oxo-2H-1-benzopyran-7-yl]-10-methoxy-6-oxaspiro[4,5]decan-9-yl Stage A: [3'aR-(3'a.α.,4'α.,7'α.,7'a.α.) ]-N-[4-Hydroxy-7-[(7'-methoxy-2'-oxo-tetrahydro-spiro[cyclopentane-1,6' [6H-1,3]dioxolo[4,5-c]pyran]-4'-yl)oxy]-8-methyl-2-oxo-2H-1-benzopyran-3-yl]-2-methyl-propanamide A solution of 810 mg of the product of Stage C of the previous example namely [3'aR-(3'a.α.,4'α.,7'α.,7'a.α.)]-4'-[[4-hydroxy-8-methyl-3-phenylazo)-2-oxo-2H-1-benzopyran-7-yl]oxy]-7'-methoxy-tetrahydro-spiro [cyclopentane-1,6'[6H-1,3]dioxolo-[4,5-c]pyran]-2'-one is subjected to hydrogenation for 2 hours under an $H_2$ atmosphere in the presence of palladium on carbon in order to obtain the corresponding 3-amino product. The reaction medium is filtered, rinsed with THF and the solvent is evaporated off. 10 ml of methylene chloride, 240 μl of triethylamine then 165 μl of isopropylic acid chloride at 0° C. are added. Agitation is carried out for 1 hour at 0° C. diluting with methylene chloride followed by washing with sodium acid phosphate and chromatography on silica eluting with a hexane/ethyl acetate mixture 2-1 and 680 mg of sought product is obtained.

Stage B: [7R-(7.α.,8β.,9β.,10.α)]-(2-Propynyloxy)-carbamate of 7-[4-Hydroxy-8-methyl-3-[(2-methyl-1-oxo-propyl)amino]-2-oxo-2H-1-benzopyran-7-yl]-10-methoxy-6-oxaspiro[4,5]decan-9-yl A solution containing 680 mg of the product of the previous stage, 1.4 g of o-propargyl hydroxylamine and 139 mg of lithium perchlorate and 6 ml of pyridine is agitated at ambient temperature for 2.5 days. The reaction solution is poured into a 10% aqueous solution of sodium hydrogen sulphate and extraction is carried out with a hexane ethyl acetate mixture 1-1. The organic phase is dried and the solvents are evaporated off. The product obtained is chromatographed on silica eluting with a methylene chloride/ ethyl acetate/acetic acid mixture 80-20-1 and 310 mg of sought product is obtained.

EXAMPLES OF PHARMACEUTICAL COMPOSITIONS

Tablets were prepared containing:

Product of Example 10 150 mg
Excipient q.s.f. 1 g
Detail of the excipient: starch, talc, magnesium stearate
Product of Example 11 150 mg
Excipient q.s.f. 1 g
Detail of the excipient: starch, talc, magnesium stearate
Injectable solutions were also prepared from the salified products.

PHARMACOLOGICAL STUDY OF THE PRODUCTS OF THE INVENTION

A—Method of Dilutions in a Liquid Medium

A series of tubes was prepared in which the same quantity of sterile nutritive medium is distributed. Increasing quantities of the product to be studied are distributed in each tube, then each tube is seeded with a bacterial strain. After incubation for 24 hours in an oven at 37° C., the growth inhibition is evaluated by transillumination which allows the minimum inhibitory concentrations (M.I.C) to be determined, expressed in micrograms/cm$^3$.

Activity in Vitro

MIC in μg/ml

On the following strains:

|  |  | EX. 10 | EX. 11 |
|---|---|---|---|
| Staph. aureus | 011HT18 | ≦0.04 | ≦0.04 |
| Staph. epidermidis | 0126042 | ≦0.04 | ≦0.04 |
| Staph. Coag. Negative | 012HT5 | 0.08 | 0.15 |
| Strepto. pyogene | 02A1UC1 | 0.16 | 0.08 |
| Strepto pneumoniae | 030BI2 | ≦0.04 | ≦0.04 |
| Entero faecium | 02D3IP2 | 0.63 | 0.32 |
| Entero faecalis | 02D2UC5 | 1.2 | 0.63 |

The products of the examples and in particular the products of Examples 10 and 11 have an excellent activity.

B—Inhibition of Gyrase B

The products are inhibitors of gyrase B; the dose at 50% of DNA supercoiling is lower than 5 μg/ml.

What is claimed is:

1. A compound of the formula

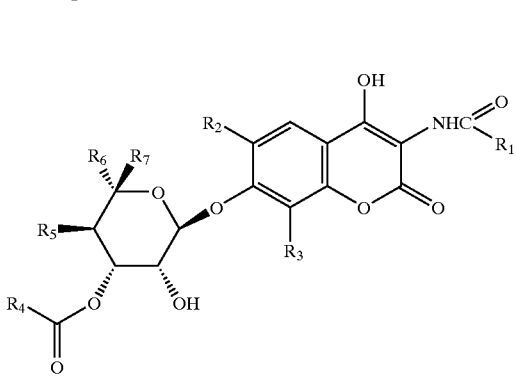

I wherein
- R$_1$ is selected from the group consisting of acyclic and cyclic alkyl, alkenyl, alkynyl, O-alkyl, O-alkenyl and O-alkynyl of up to 8 carbon atoms unsubstituted or substituted by at least one halogen and, optionally interrupted by oxygen or sulfur or nitrogen, unsubstituted or substituted aryl or aralkyl of up to 18 carbon atoms, an unsubstituted or substituted mono or polycyclic aromatic or non-aromatic heterocyclic, —NH$_2$, —NHalk$_1$ and —NHOalk$_2$ alk$_1$, and alk$_2$ are alkyl of up to 8 carbon atoms,
- R$_2$ is hydrogen or halogen,
- R$_3$ is selected from the group consisting of hydrogen, alkyl of up to 8 carbon atoms, and halogen,
- R$_4$ is selected from the group consisting of —NHR' and —NHOR" in which R' or R" are individually selected from the group consisting of acyclic and cyclic, alkyl, alkenyl and alkynyl of up to 8 carbon atoms and unsubstituted or substituted aryl of up to 14 carbon atoms,
- R$_5$ is hydrogen or alkoxy of up to 8 carbon atoms,
- R$_6$ is alkyl or CH$_2$O-alkyl, in which alkyl is alkyl of up to 8 carbon atoms,
- R$_7$ is a hydrogen or a alkyl of up to 8 carbon atoms or R$_6$ and R$_7$ together with the carbon which carries them form a ring and its pharmaceutical addition salts with bases.

2. A compound of claim 1 in which R$_1$ is an alkyl of up to 4 carbon atoms.

3. A compound of claim 2 in which R$_1$ is

4. A compound of claim 1 wherein R$_1$ is phenyl.
5. A compound of claim 1 wherein R$_2$ is hydrogen.
6. A compound of claim 1 wherein R$_3$ methyl.
7. A compound of claim 1 wherein R$_5$ OCH$_3$.
8. A compound of claim 1 wherein R$_6$ and R$_7$ are methyl.
9. A compound of claim 1 wherein R$_6$ and R$_7$ are ethyl.
10. A compound of claim 1 wherein R$_6$ and R$_7$ together with the carbon which carry them form cyclopentyl.
11. A compound of claim 1 wherein R$_4$ is —NH—O—CH$_2$—C=CH.

12. A compound of claim 1 which is:
[7R-(7.α.,8β.,9β., 10.α)]-(2-propynyloxy)-carbamate of 8-hydroxy-7-[4-hydroxy-8-methyl-2-oxo-3-(benzoylamino)-2H-1-benzopyran-7-yl]-10-methoxy-6-oxaspiro[4,5]decan-9-yl.

13. A compound of claim 1 which is: [7R-(7.α.,8β.,9β., 10.α)]-(2-propynyloxy)-carbamate of 7-[4-hydroxy-8-methyl-3-[(2-methyl-1-oxo-propyl)amino]-2-oxo-2H-1-benzopyran-7-yl]-10-methoxy-6-oxaspiro[4,5]decan-9-yl.

14. As medicaments the compound of claim 12 and its addition salts with pharmaceutically acceptable bases.

15. The pharmaceutical compositions containing as active ingredient at least one medicament defined in claim 14.

16. A process for the preparation of a compound of claim 1, comprising reacting a compound of the formula:

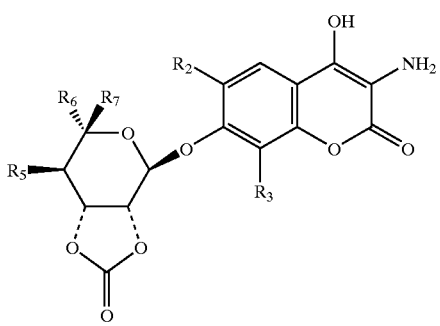

II with a compound of the formula

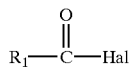

in which R$_1$ is defined as in claim 1 and Hal is halogen to obtain a compound of the formula

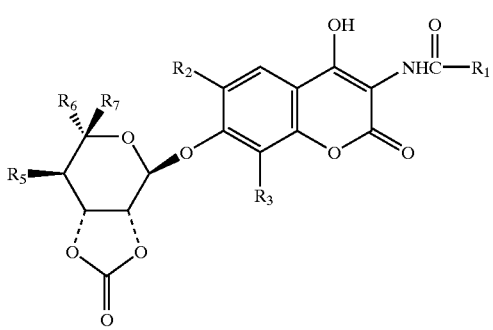

III reacting the compound of Formula III with a compound of the formula:

R$_4$H

IV to obtain a compound of the formula:

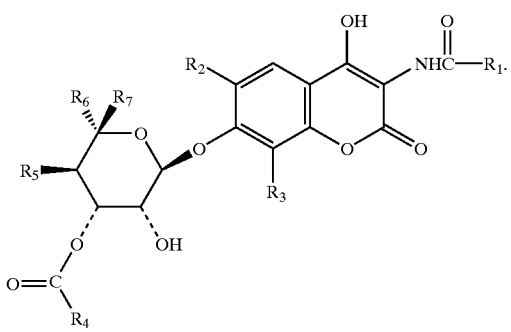

(I)

17. As new chemical products, the compounds of formula (II) and (III) defined in claim 16.

18. Variant of the process according to claim 16 characterized in that a compound of formula (V):

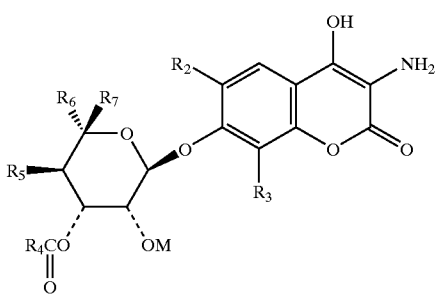

(V)

in which the substituents retain their previous meaning and OM represents a blocked hydroxyl radical, is subjected to the action of a $R_1COHal$ compound, in which $R_1$ retains its previous meaning and Hal represents a halogen atom, then to the action of an agent which releases the OH function in order to obtain the corresponding compound of formula (I)

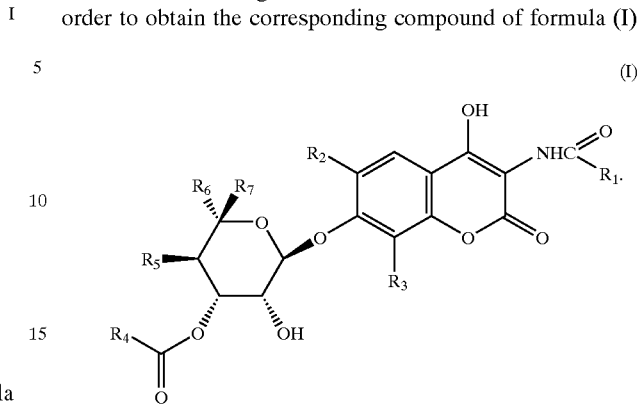

(I)

19. As new chemical products, the compounds of formula (V) defined in claim 18.

20. A method of treating bacterial infections in warm-blooded animals comprising administering to warm-blooded animals in need thereof a bacterially effect amount of a compound of claim 1.

21. The method of claim 20 wherein the compound is -[7R-(7.α., 8β., 9β., 10.α)]-(2-propynyloxy)-carbamate of 8-hydroxy-7-[4-hydroxy-8-methyl-2-oxo-3-(benzoylamino)-2H-1-benzopyran-7-yl]-10-methoxy-6-oxaspiro [4,5] decan-9-yl or [7R-(7.α., 8β., 9β., 10.α)]-(2-propynyloxy)-carbamate of 7-[4-hydroxy-8-methyl-3-[(2-methyl-1-oxo-propyl)amino]-2-oxo-2H-1-benzopyran-7-yl]-10-methoxy-6-oxaspiro [4,5] decan-9-yl.

* * * * *